(12) United States Patent
Dreyfuss et al.

(10) Patent No.: US 12,133,630 B2
(45) Date of Patent: Nov. 5, 2024

(54) SURGICAL SHEATH SYSTEM

(71) Applicant: ARTHREX, INC., Naples, FL (US)

(72) Inventors: Peter Dreyfuss, Naples, FL (US); Ryan A. Kellar, Naples, FL (US); Chad Lavender, Hurricane, WV (US); Matthew Daggett, Leawood, KS (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/584,913

(22) Filed: Jan. 26, 2022

(65) Prior Publication Data

US 2023/0233066 A1    Jul. 27, 2023

(51) Int. Cl.
*A61B 1/00*     (2006.01)
*A61B 1/05*     (2006.01)
(Continued)

(52) U.S. Cl.
CPC ...... *A61B 1/00154* (2013.01); *A61B 1/00137* (2013.01); *A61B 1/05* (2013.01);
(Continued)

(58) Field of Classification Search
CPC ............ A61B 1/00064; A61B 1/00066; A61B 1/00071; A61B 1/0008; A61B 1/00087; A61B 1/00096; A61B 1/00101; A61B 1/00105; A61B 1/00131; A61B 1/00133; A61B 1/00135; A61B 1/00154; A61B 1/05; A61B 17/1703; A61B 17/17; A61B 17/3421; A61B 17/3423; A61B 17/3472; A61B 17/3476; A61B 17/3478; A61B 2017/3445; A61B 17/00234; A61B 2017/00292; A61B 2017/00296; A61B 2017/00336; A61B 2017/0034; A61B 2017/3415; A61B 2017/3417; A61B 2017/3421; A61B 1/00142; A61B 1/00137–0014; A61B 1/012; A61B 1/0125; A61B 17/34; A61B 2017/3449; A61B 2017/345; A61B 2017/3468;
(Continued)

(56) References Cited

U.S. PATENT DOCUMENTS

2001/0053873 A1    12/2001    Schaaf et al.
2002/0013608 A1*   1/2002    ElAttrache ............ A61F 2/0811
                                                                    606/232
(Continued)

FOREIGN PATENT DOCUMENTS

DE         3319049       5/1984
DE      102011053779     3/2013

OTHER PUBLICATIONS

International Search Report and Written Opinion, dated Jul. 4, 2023, pp. 1-25.

*Primary Examiner* — Ryan N Henderson
*Assistant Examiner* — Pamela F Wu
(74) *Attorney, Agent, or Firm* — KARISH & BJORGUM, PC

(57) ABSTRACT

A surgical sheath system having a sheath with a hollow shaft; and a head coupled to and in fluid communication with the hollow shaft, the head having a first mounting feature for coupling a first surgical device; and a second mounting feature for coupling a second surgical device, the second surgical device being a different type of surgical device than the first surgical device.

10 Claims, 5 Drawing Sheets

(51) Int. Cl.
*A61B 17/17* (2006.01)
*A61B 17/34* (2006.01)
*A61B 17/04* (2006.01)

(52) U.S. Cl.
CPC ...... *A61B 17/1703* (2013.01); *A61B 17/3423* (2013.01); *A61B 2017/0409* (2013.01)

(58) Field of Classification Search
CPC .... A61B 2017/3474; A61B 2017/3476; A61B 2017/3478; A61B 2017/0409; A61B 1/018; A61B 2017/320775; A61B 17/320016; A61B 2017/320028; A61B 2017/320056
USPC ........ 600/104, 109, 112, 121–123, 125, 130, 600/136, 137, 153, 155, 156, 160, 172; 606/79–99
See application file for complete search history.

(56) References Cited

U.S. PATENT DOCUMENTS

| | | |
|---|---|---|
| 2005/0124988 A1 | 6/2005 | Terrill-Grisoni et al. |
| 2007/0260255 A1* | 11/2007 | Haddock ............ A61B 17/3472 606/184 |
| 2008/0154304 A1* | 6/2008 | Crawford ........... A61B 17/8819 206/572 |
| 2010/0217080 A1 | 8/2010 | Cheung et al. |
| 2012/0010464 A1* | 1/2012 | Adams .................. A61B 1/303 600/156 |
| 2016/0015253 A1* | 1/2016 | Roop .................... A61B 1/3132 600/109 |
| 2018/0132891 A1 | 5/2018 | Cappelleri et al. |
| 2021/0228244 A1* | 7/2021 | Wall ................... A61B 17/7092 |
| 2021/0361151 A1 | 11/2021 | Kellar et al. |
| 2022/0079625 A1* | 3/2022 | Einarsson ............ A61B 1/0607 |

\* cited by examiner

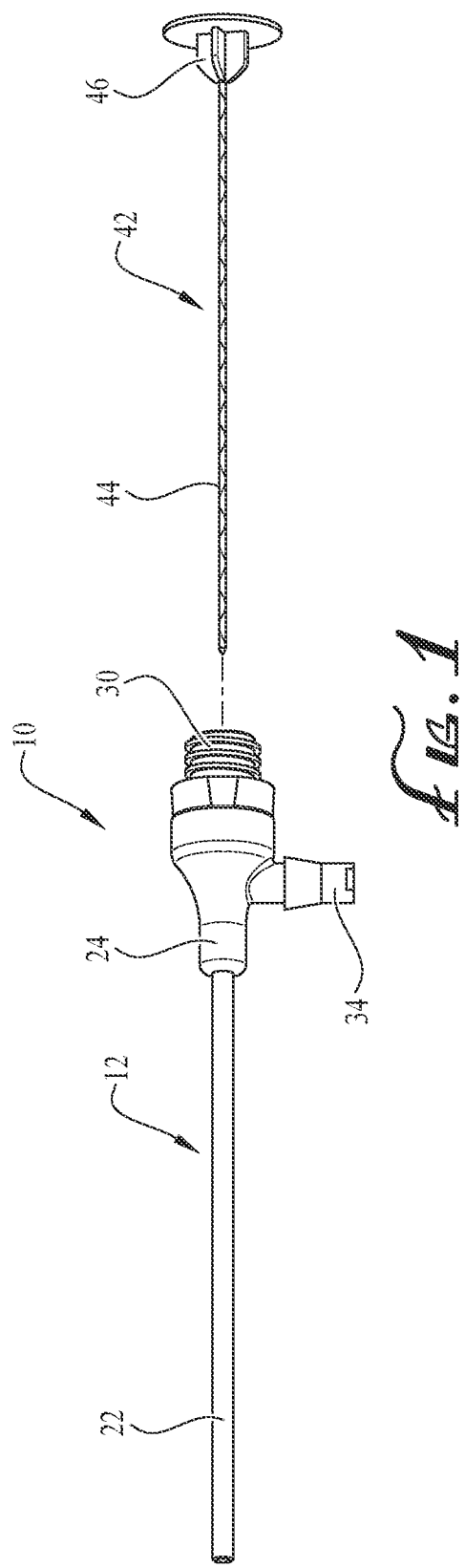
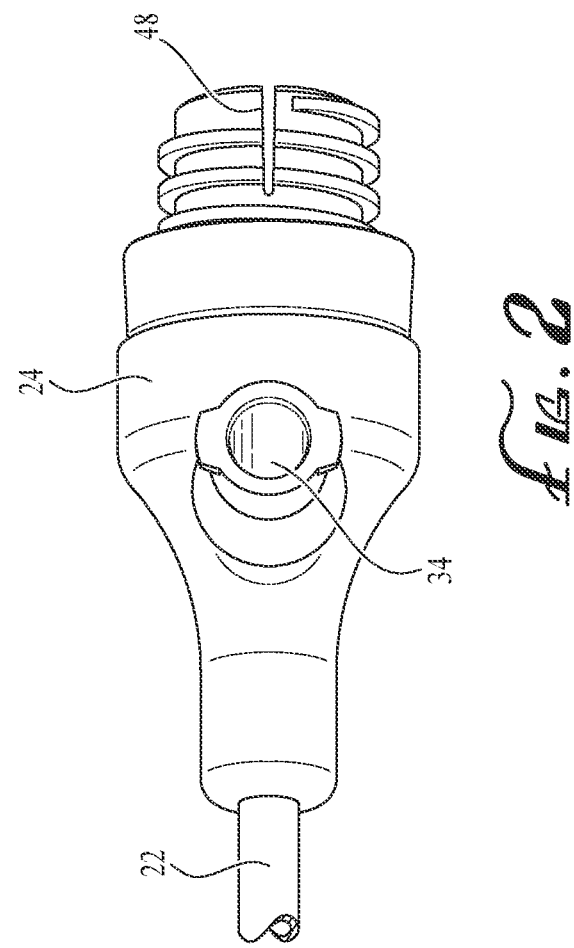

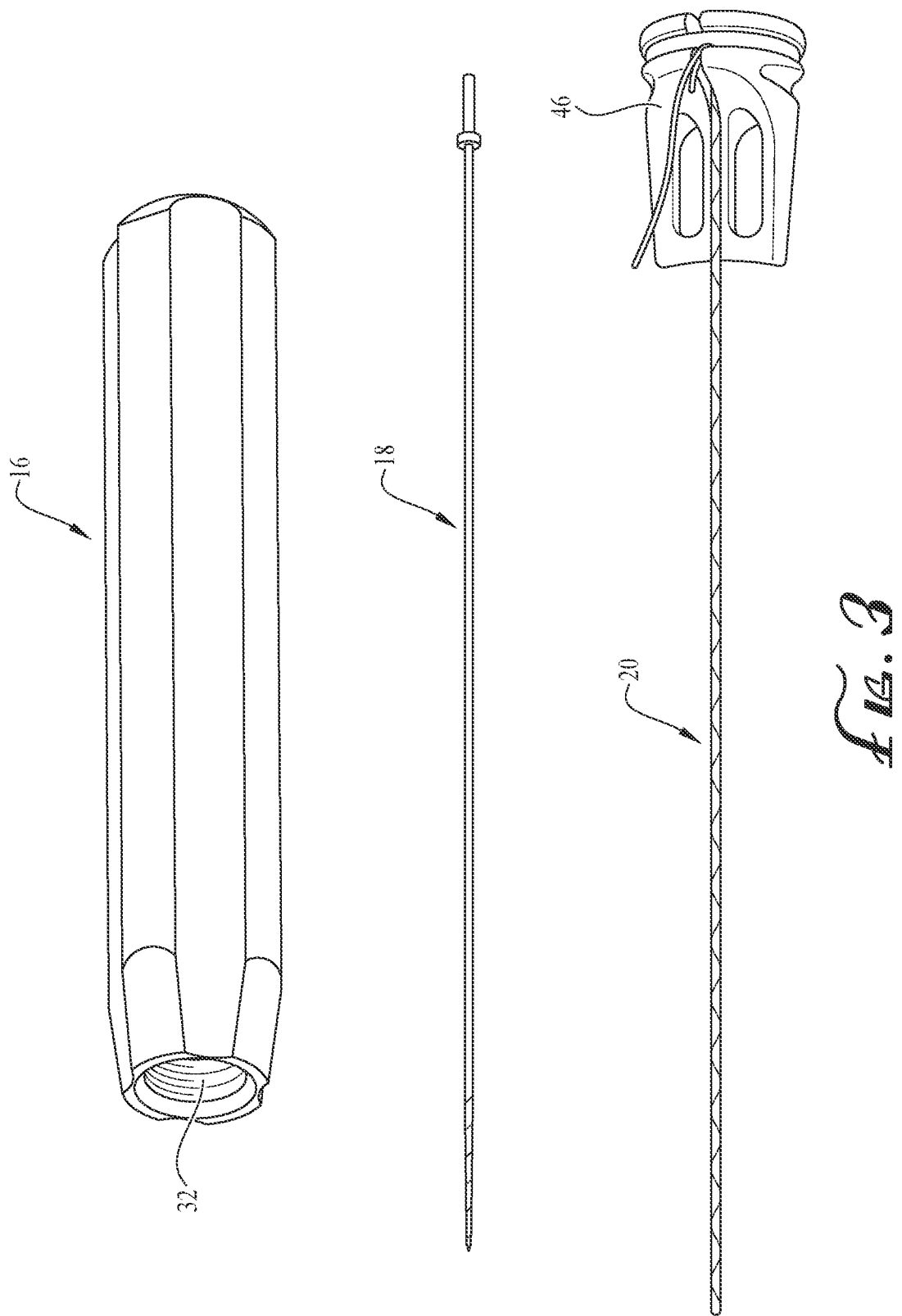

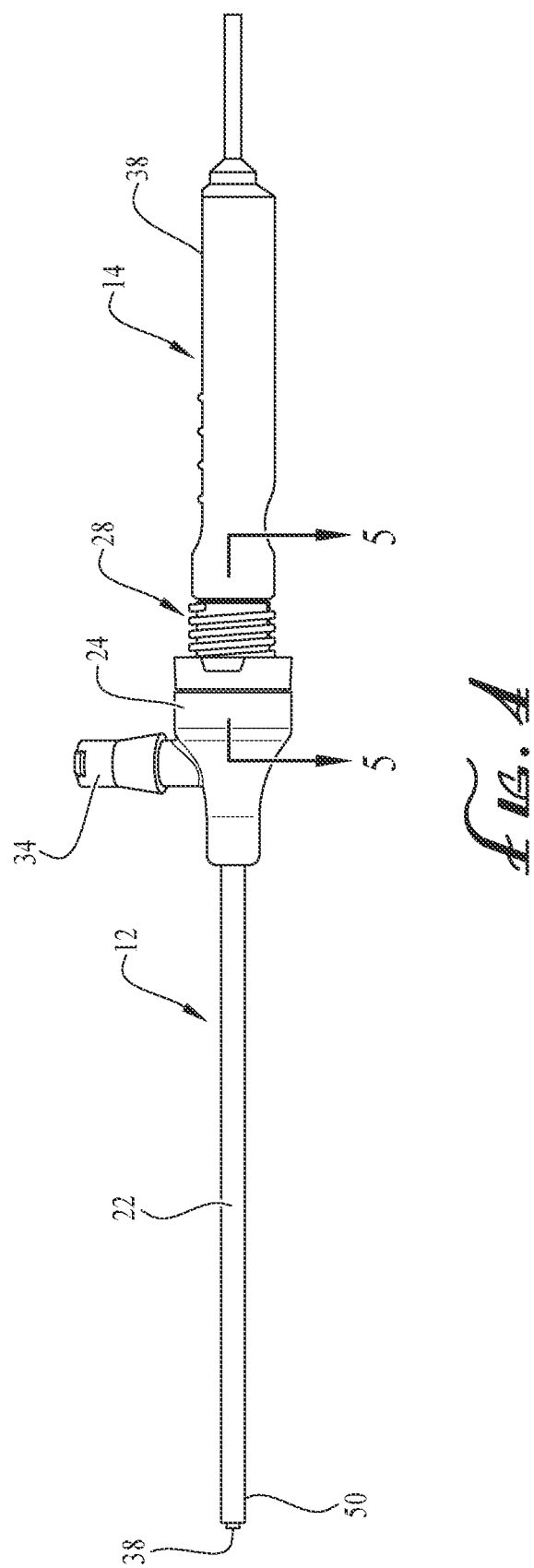

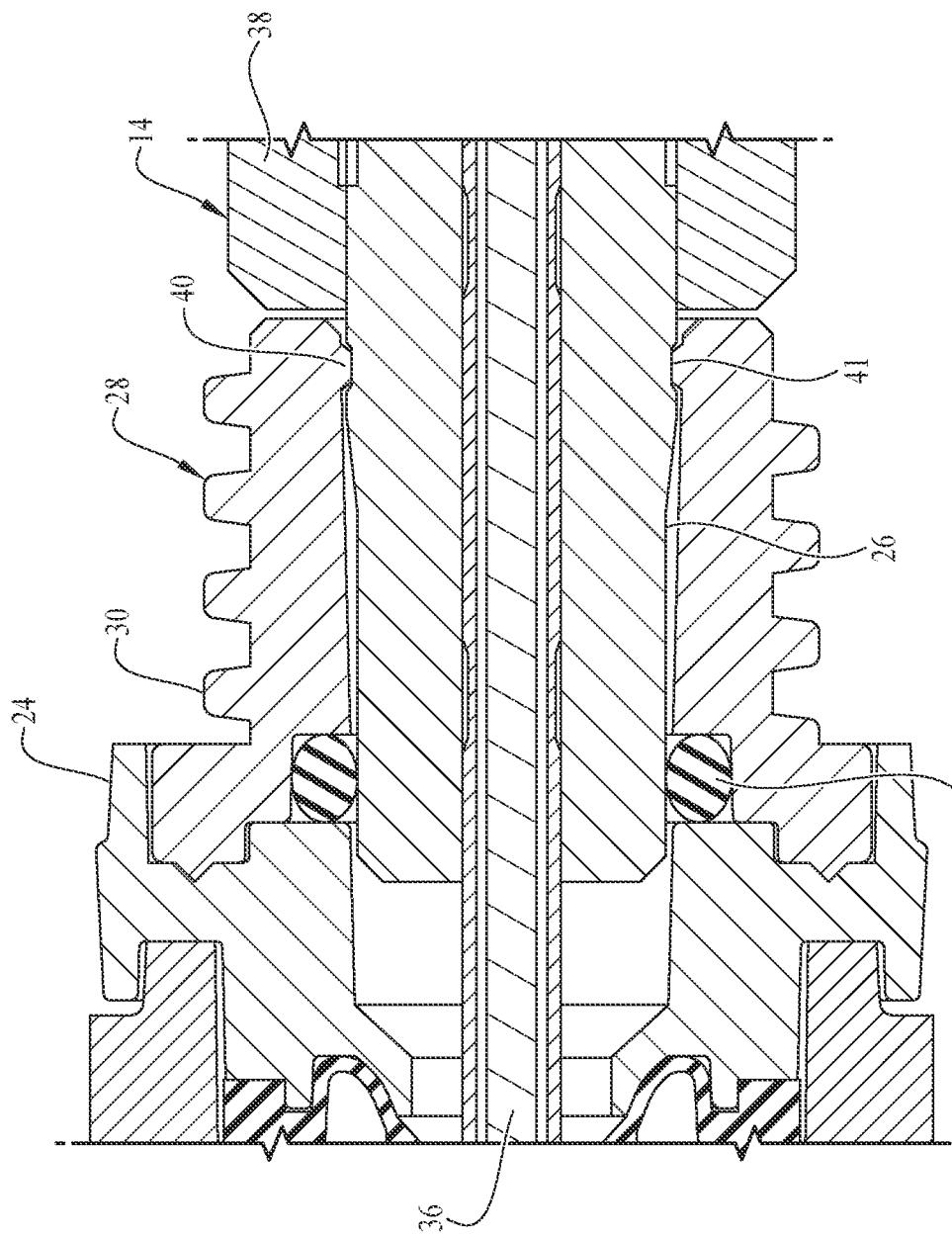

SURGICAL SHEATH SYSTEM

BACKGROUND

The present disclosure relates to devices used in endoscopic surgery and, more particularly, to a surgical sheath system where the same inflow sheath may be used with endoscopic cameras and other surgical tools.

Current surgical systems typically utilize one inflow sheath for use with an endoscopic camera and one or more additional sheaths for drilling and suturing at a surgical site. This requires that a user approximate the location of the drill or suture location which is difficult and may lead to errors.

Accordingly, there exists a need for a system and method of visualizing a surgical site that remedies the shortcomings of the prior art.

SUMMARY

According to implementations, the present disclosure is directed to a surgical sheath system having a sheath. The sheath has a hollow shaft; and a head coupled to and in communication with the hollow shaft. The head has a first mounting feature for mounting a first surgical device; and a second mounting feature for mounting a second surgical device, the second surgical device being a different type of surgical device than the first surgical device.

The sheath may have an opening and the first mounting feature may be a detent. The first surgical device may be an endoscopic camera and the endoscopic camera may be a mounting structure corresponding to the detent so that the camera is removably fixable in the sheath. The surgical sheath may have a seal in the opening, the seal configured to form a fluid tight seal against the endoscopic camera when the endoscopic camera is mounted within the sheath. Optionally, the seal is an o-ring and is further configured to hinder axial rotation of the endoscopic camera relative to the sheath. Optionally, the sheath has a fluid interface in fluid communication with the shaft.

In an implementation, the surgical sheath system also has a drill guide couplable to the second mounting feature. In an implementation, the surgical sheath system also has at least one drill removably insertable in the drill guide. In an implementation, the surgical sheath system also has at least one anchor positioner removably insertable in the drill guide. In an implementation, the surgical sheath system also has at least one obturator removably mountable within the sheath.

Optionally, the second mounting feature has a plurality of threads on an outer surface of the head, and the drill guide has a distal end with a threaded opening configured to engage the threads on the outer surface of the head. Optionally, the second mounting feature further comprises at least one opening in the threads configured for managing sutures.

A surgical sheath system according to an implementation has: a sheath; a camera removably couplable to the sheath; a drill guide removably couplable to the sheath; and a drill removably insertable into the drill guide. In an implementation, the surgical sheath system has at least one anchor positioner insertable into the drill guide. In an implementation, the surgical sheath system also has an obturator insertable into the sheath.

The sheath may have a fluid interface. The sheath and the camera may be configured with a detent to removably couple the camera to the sheath. The sheath and the drill guide may be configured with corresponding threads to removably couple the drill guide to the sheath.

In an implementation, this disclosure is directed to a surgical method having the steps of: inserting a camera in a sheath and visualizing a surgical site; removing the camera from the sheath; coupling a drill guide to the sheath; inserting a drill through the drill guide and the sheath and drilling a hole; and removing the drill from the sheath. The surgical method may also have the steps of: inserting an obturator in the sheath; positioning the sheath in a patient; and removing the obturator from the sheath. The surgical method may also have the steps of: inserting an anchor positioner into the drill guide and the sheath; placing at least one anchor in the surgical site; and withdrawing the anchor positioner from the drill guide and the sheath.

These and other features are described below.

BRIEF DESCRIPTION OF THE DRAWINGS

The features, aspects and advantages of the present invention will become better understood with regard to the following description, appended claims and accompanying figures wherein:

FIG. 1 is side elevation view of a sheath and an obturator usable with the sheath according to an implementation;

FIG. 2 is an additional side elevation view of the sheath of FIG. 1;

FIG. 3 is a side elevation view of drill guide, drill and anchor positioner usable with the sheath of FIG. 1 according to an implementation;

FIG. 4 is a side elevation view of a sheath and endoscopic camera according to an implementation;

FIG. 5 is a cross sectional elevation view of a portion of FIG. 4;

DETAILED DESCRIPTION

Figure 6A:
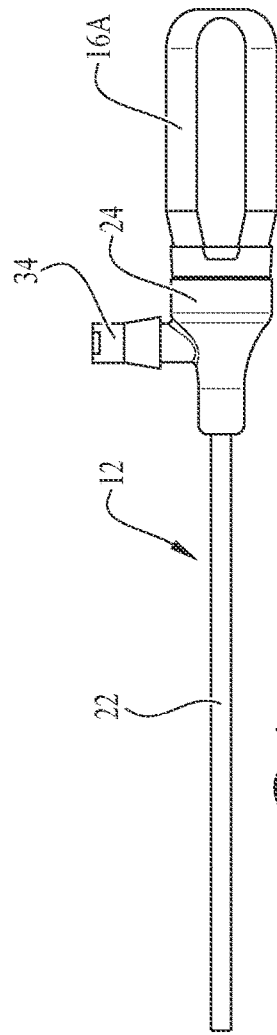
FIG. 6A is a side elevation view of a guide handle coupled to a sheath for use in ankle surgery according to an implementation.

In the following description of the preferred implementations, reference is made to the accompanying drawings which show by way of illustration specific implementations in which the invention may be practiced. Wherever possible, the same reference numbers will be used throughout the drawings to refer to the same or like parts. It is to be understood that other implementations may be utilized and structural and functional changes may be made without departing from the scope of this disclosure.

FIGS. 1 to 6C show a surgical sheath system 10 according to implementations of the present disclosure. The surgical sheath system 10 has a sheath 12 that is compatible with at least two different surgical devices. In an implementation, at least one of the surgical devices is a camera 14, such as an endoscopic camera. In an implementation, at least one of the surgical devices is a drill guide 16. As shown in FIG. 3, the drill guide 16 may be used in conjunction with, for example, a drill 18 and an anchor positioner 20 (which may also be referred to as an anchor spear). Other surgical devices may be used with the sheath 12, such as for example and without limitation, a resection device.

In an implementation, the drill guide 16 is configured to allow a drill to reach a preselected depth beyond a distal end of the sheath 12 when the drill guide is coupled to the sheath and the drill is completely inserted into the drill guide. For example, the drill guide 16 may be usable with drills for the Arthrex Fibertech anchor system and Fibertech anchor positioners. Because the length of the sheath 12 is known, specific drill guides 16 may be selected with lengths that allow for the use of existing drills.

In an implementation, the sheath 12 has a hollow shaft 22 coupled to and in fluid communication with a head 24. The head 24 has an opening 26 with at least one feature for mounting the camera 14 as will be described in more detail below. The head 24 also has at least one feature 28 for mounting a surgical device. In an implementation, the feature 28 is a plurality of threads 30 that mate with corresponding threads on the surgical tool being connected. In an implementation, as shown in FIGS. 1 and 3, the drill guide 16 has a plurality of threads 32 that mate with threads 30 on the sheath 12. Optionally, a camera holder may be threaded onto the sheath threads 30 prior to insertion of the endoscopic camera 14 for hands free placement of the camera. In additional implementations, the feature 28 for mounting a surgical device is a j-lock or clip-on connection.

In an implementation, the sheath head 24 has a fluid interface 34 in communication with the shaft 22 and the head 24. The fluid interface 34 may be coupled to a fluid source (not shown) to provide fluid to a surgical site. Alternatively, the fluid interface 34 may be coupled to a vacuum source (not shown) to help remove fluid from a surgical site. The sheath 12 may have a straight shaft 22. Alternatively, the shaft 22 may have a bend.

In an implementation, as shown in FIGS. 4 and 5, the camera 14 has a shaft 36 and a handle 38 coupled to the shaft. The sheath 12 and the camera 14 are configured so that the camera shaft 36 extends though the sheath shaft 22 and a portion of the camera handle 38 mounts within the sheath opening 26. In an implementation, the sheath opening 26 has a detent 40. The detent 40 is configured to removably engage with a mounting feature 41, such as a groove, on the camera handle 38 when the camera 14 is fully inserted into the sheath 12 to securely couple the camera to the sheath. In additional implementations other features, such as, for example, magnets, a j-lock feature and a bumper with indexing may be used to couple the camera 14 to the sheath 12.

The sheath 12 may also have a seal 43, such as an o-ring, positioned inside the opening 26. In an implementation, the seal 43 is configured so that when the camera 14 is inserted into the sheath 12, the seal contacts both the sheath and the camera to form a proximal fluid tight seal and to prevent axial rotation of the camera relative to the sheath.

In an implementation, when the camera 14 is fully inserted into the sheath 12, a distal end 38 of the camera shaft 36 extends a minimal distance from the sheath shaft 22 to allow for imaging. In an implementation, the distal end of the camera shaft 36 extends less than about 0.10" inch from the sheath shaft 22, and more preferably less than about 0.05" inch, and more preferably less than about 0.03" inch. A distal end 50 of the sheath shaft 22 may have a blunt edge to minimize trauma.

An obturator 42 may be used to facilitate insertion of the sheath into a patient. The obturator 42 may have a shaft 44 coupled to a head 46. A distal end of the shaft 44 may be pointed or blunt. The obturator is inserted until the obturator head 46 contacts the sheath head 24. The distal end of the obturator shaft 44 then extends from the end of the sheath shaft 22. The obturator head 46 may be impacted, such as with a mallet to aid in insertion of the sheath 12 into a patient. Once the sheath has been inserted to a desired depth, the obturator may be withdrawn and another surgical device connected to the sheath 12.

Instead of the obturator 42, or after the obturator has been withdrawn, a user can connect the camera 14 to the sheath 12 and insert the sheath into a patient. The user can then use the camera 14 to position the sheath 12 at a precise surgical location for further manipulation, such as drilling. The user can then remove the camera 14 and couple other surgical devices, such as the drill guide 16 to the sheath 12.

After connection of the drill guide 16, the drill 18 may be used to drill a hole into the appropriate structure. After drilling is complete, the drill 18 may be removed and the anchor positioner 20 inserted into the drill guide 16. In an implementation, the anchor positioner 20 has a handle 46 that may be impacted, such as with a mallet, to insert an anchor into a hole made by the drill 18. In an implementation, the drill guide 16 and anchor positioner 20 are configured so that the anchor positioner may be impacted until the handle 46 is flush with a proximal end of the drill guide to properly insert the anchor. The handle 46 is then pulled back to set the anchor in the bone. Following insertion of the anchor, the anchor positioner 20 is removed.

The anchor is coupled to surgical suture and surgical suture may be manipulated for surgical fastening within a patient. In an implementation, the suture is freed from the anchor positioner handle 46 by removing a suture release tab. In an implementation, as shown in FIG. 2, the sheath head 24 has at least one suture opening 48 for manipulation of suture. In an implementation, the sheath head 24 has a plurality of suture openings 48 for manipulation of suture. An additional endoscopic camera may be inserted to further visualize surgical procedures, such as drilling and suturing.

Pre-selected combinations of components may be placed in a contained surgical instrument pack for specific surgical procedures, such as for ankle repair, shoulder repair or hip repair. FIG. 6A shows a drill guide 16A usable in ankle surgery coupled to the sheath 12. The drill guide 16A may be configured for use with, for example and without limitation, a 1.6 mm GuideWire, a 1.35 mm GuideWire, 1.3 mm Suture Tape and #1FiberWire. In an implementation, for use in ankle surgery, the shaft 22 has a length of between about 0.5 inches and 2.5 inches, and more preferably between about 0.6 inches and about 2.0 inches. In an implementation, for use in ankle surgery, the drill guide 16A has a length of between about 1 inch and about 2 inches, and more preferably between about 1.4 inches and 1.6 inches. In an implementation, for use in ankle surgery, the overall length of the sheath 12 coupled to the drill guide 16A is between about 6 inches and about 7 inches, and more preferably about 6.5 inches.

Figure 6B:
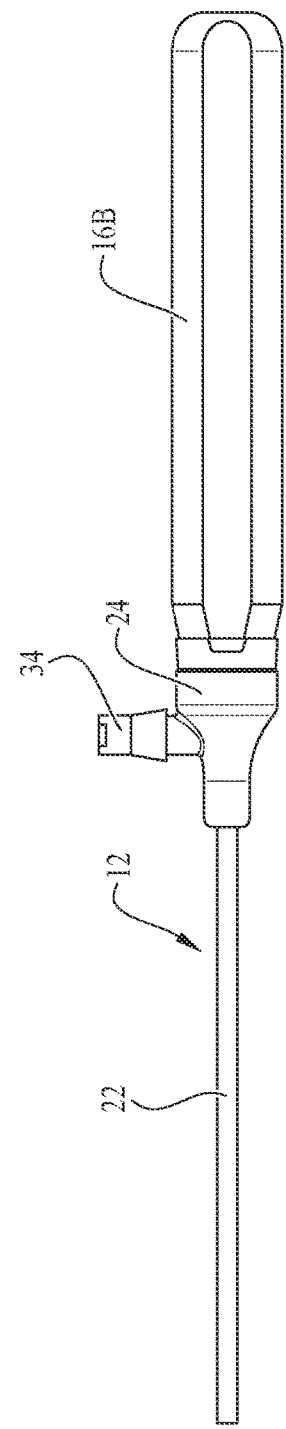
FIG. 6B is a side elevation view of a guide handle coupled to a sheath for use in shoulder surgery according to an implementation.

FIG. 6B shows a drill guide 16B usable in shoulder surgery coupled to the sheath 12. The drill guide 16B may be configured for use with, for example and without limitation, a 1.8 mm drill, and a 1.8 mm FiberTak suture anchor. In an implementation, for use in shoulder surgery, the shaft 22 has a length of between about 3 inches and 5 inches, and more preferably between about 3.5 inches and about 4.5 inches, and more preferably between about 3.7 inches and 3.8 inches. In an implementation, for use in shoulder surgery, the drill guide 16B has a length of between about 3 inches and about 5 inches, and more preferably between about 3.5 inches and 4.5 inches, and more preferably about 4 inches. In an implementation, for use in shoulder surgery, the overall length of the sheath 12 coupled to the drill guide 16B is between about 8 inches and about 10 inches, and more preferably about 9 inches.

Figure 6C:
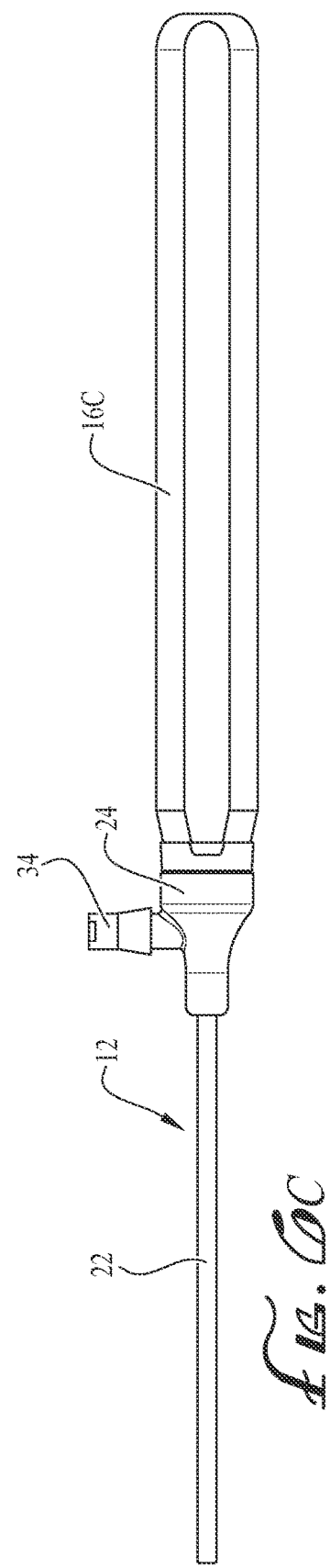
FIG. 6C is a side elevation view of a guide handle coupled to a sheath for use in hip surgery according to an implementation.

FIG. 6C shows a drill guide 16C usable in hip surgery coupled to the sheath 12. The drill guide 16C may be configured for use with, for example and without limitation, a 1.6 mm drill, a 1.7 mm or a 1.8 mm drill, 1.3 mm SutureTape. In an implementation, for use in hip surgery, the shaft 22 has a length of between about 5 inches and 7 inches, and more preferably between about 5.5 inches and about 6.5 inches, and more preferably about 6 inches. In an implementation, for use in hip surgery, the drill guide 16C has a length of between about 5 inches and 7 inches, and more preferably between about 5.5 inches and about 6.5 inches, and more preferably about 6 inches. In an implementation, for use in hip surgery, the overall length of the sheath 12 coupled to the drill guide 16C is between about 12 inches and about 14 inches, and more preferably about 13 inches.

In a further implementation, the sheath 12 may have a camera positioned on an outside of the shaft 22 to allow for visualization of a surgical site while other surgical devices are being used with the sheath. This may allow a surgeon to avoid inserting more than one sheath and camera into a patient to reduce risk and patient trauma.

The sheath discussed herein is highly advantageous in that it is a single sheath that allows a surgeon to view surgical site, introduce fluid into or remove fluid from a surgical site and manipulate surgical devices at a surgical site. For example, the sheath may be used with a camera, drill guide, drill, and an anchor and suture positioner. Additionally, the external threads 30 allow for calibrated drill guides to be attached to each length of sheath depending on procedure to be performed. The suture openings 48 in the sheath advantageously allow for suture manipulation after withdrawal of the drill guide 16.

There is disclosed in the above description and the drawings, a surgical sheath system that fully and effectively overcomes the disadvantages associated with the prior art. However, it will be apparent that variations and modifications of the disclosed implementations may be made without departing from the principles of the invention. The presentation of the implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. A surgical sheath system comprising:
    a sheath further comprising:
        a hollow shaft; and
        a head coupled to and in communication with the hollow shaft, the head further comprising an opening; a head mating feature inside the opening; and a plurality of threads on an outer surface, wherein the plurality of threads surround the opening of the head;
    a camera removably couplable to the sheath, the camera further comprising a camera mating feature configured to mate with the head mating feature in the sheath head to removably couple the camera to the the sheath, wherein one of the head mating feature and the camera mating feature comprises a detent and the other of the head mating feature and camera mating feature comprises a slot;
    a drill guide removably couplable to the sheath, the drill guide further comprising a distal end comprising a threaded opening configured to engage with the plurality of threads on the outer surface of the sheath head to removably couple the drill guide to the sheath; and
    a drill removably insertable into the drill guide.

2. The surgical sheath system of claim 1, further comprising at least one anchor positioner insertable into the drill guide.

3. The surgical sheath system of claim 1, further comprising an obturator insertable into the sheath.

4. The surgical sheath system of claim 1, wherein the sheath further comprises a fluid interface in fluid communication with the shaft.

5. The surgical sheath system of claim 1 further comprising a seal in the sheath head opening, the seal configured to form a fluid tight seal against the endoscopic camera when the endoscopic camera is mounted within the sheath.

6. The surgical sheath system of claim 5, wherein the seal further comprises an o-ring and is further configured to hinder axial rotation of the camera relative to the sheath.

7. The surgical sheath system of claim 1, wherein the sheath head further comprises at least one slot configured for managing sutures.

8. A surgical method comprising the steps of:
    selecting a camera comprising a camera mating feature;
    selecting a drill guide comprising a distal end comprising a threaded opening;
    selecting a sheath comprising:
        a hollow shaft; and
        a head coupled to and in communication with the hollow shaft, the head further comprising an opening; a head mating feature inside the opening configured to mate with the camera mating feature for removably mounting the camera in the sheath, wherein one of the head mating feature and the camera mating feature comprises a detent and the other of the head mating feature and camera mating feature comprises a slot; and a plurality of threads on an outer surface, wherein the plurality of threads surround the opening of the head;
    inserting the camera in the sheath until the camera mating feature engages the head mating feature and visualizing a surgical site;
    removing the camera from the sheath;
    coupling the drill guide to the sheath using the plurality of threads on the sheath and the threaded opening of the drill guide;
    inserting a drill through the drill guide and the sheath and drilling a hole; and
    removing the drill from the sheath.

9. The surgical method of claim 8, further comprising the steps of:
    inserting an obturator in the sheath;
    positioning the sheath in a patient; and
    removing the obturator from the sheath.

10. The surgical method of claim 8, further comprising the steps of:
    inserting an anchor positioner into the drill guide and the sheath;
    placing at least one anchor in the surgical site; and
    withdrawing the anchor positioner from the drill guide and the sheath.

* * * * *